(12) United States Patent
Ricoul

(10) Patent No.: US 9,933,398 B2
(45) Date of Patent: Apr. 3, 2018

(54) DEVICE AND METHOD FOR EXTRACTING COMPOUNDS CONTAINED IN A LIQUID SAMPLE WITH A VIEW TO ANALYSING THEM

(71) Applicant: COMMISSARIAT A L'ENERGIE ATOMIQUE ET AUX ENE ALT, Paris (FR)

(72) Inventor: Florence Ricoul, Quaix-en-Chartreuse (FR)

(73) Assignee: Commissariat à l'énergie atomique et aux énergies alternatives, Paris (FR)

( * ) Notice: Subject to any disclaimer, the term of this patent is extended or adjusted under 35 U.S.C. 154(b) by 483 days.

(21) Appl. No.: 14/389,051

(22) PCT Filed: Mar. 28, 2013

(86) PCT No.: PCT/EP2013/056798
§ 371 (c)(1),
(2) Date: Sep. 29, 2014

(87) PCT Pub. No.: WO2013/144330
PCT Pub. Date: Oct. 3, 2013

(65) Prior Publication Data
US 2015/0068280 A1    Mar. 12, 2015

(30) Foreign Application Priority Data
Mar. 29, 2012   (FR) ...................................... 12 52850

(51) Int. Cl.
*G01N 30/14*   (2006.01)
*G01N 1/40*    (2006.01)
(Continued)

(52) U.S. Cl.
CPC ............. *G01N 30/14* (2013.01); *B01D 15/08* (2013.01); *G01N 1/405* (2013.01); *G01N 30/08* (2013.01);
(Continued)

(58) Field of Classification Search
CPC ....................................................... G01N 30/14
(Continued)

(56) References Cited

U.S. PATENT DOCUMENTS 7,552,617 B2 *   6/2009   Danilchik ................ G01N 1/28
                                                           73/19.12
7,709,267 B2 *   5/2010   Tipler ................... G01N 1/2226
                                                           422/68.1
(Continued)

FOREIGN PATENT DOCUMENTS

EP    1 867 982 A2    12/2007
EP    1 867 982 A3    12/2007
(Continued)

OTHER PUBLICATIONS

Alfeeli et al., MEMS-based multi-inlet-outlet preconcentrator coated by inkjet printing of polymer adsorbents, Sensors and Actuators B 133 (2008) pp. 24-32.*
(Continued)

*Primary Examiner* — Paul West
(74) *Attorney, Agent, or Firm* — Oblon, McClelland, Maier & Neustadt, L.L.P.

(57) ABSTRACT

A device for extraction of at least one analyte contained in a liquid sample, including an extraction and desorption zone of the analyte with a stationary phase as the extraction zone, a liquid supply inlet to the extraction zone, a gas supply inlet to the extraction zone, an evacuation outlet from the extraction zone that will be connected to either a collection tank, or a device for analysis of the analytes, a valve configured (Continued)

to connect the extraction zone to one of the supply inlets, a valve configured to connect the extraction zone to one of the evacuation outlets, a mechanism heating the valve zone such that when the extraction zone is supplied with liquid, evacuation from the extraction zone takes place to the collection tank.

21 Claims, 2 Drawing Sheets

(51) Int. Cl.

| | | |
|---|---|---|
| *G01N 30/08* | (2006.01) | |
| *G01N 30/12* | (2006.01) | |
| *G01N 30/38* | (2006.01) | |
| *G01N 30/60* | (2006.01) | |
| *B01D 15/08* | (2006.01) | |
| *G01N 30/00* | (2006.01) | |
| *G01N 30/02* | (2006.01) | |

(52) U.S. Cl.
CPC .......... *G01N 30/12* (2013.01); *G01N 30/38* (2013.01); *G01N 30/6095* (2013.01); *G01N 2030/009* (2013.01); *G01N 2030/025* (2013.01); *G01N 2030/085* (2013.01); *G01N 2030/385* (2013.01)

(58) Field of Classification Search
USPC .............................................. 73/23.35–23.42
See application file for complete search history.

(56) References Cited

U.S. PATENT DOCUMENTS

| | | | |
|---|---|---|---|
| 8,123,834 B2* | 2/2012 | Masel ................. | B01D 15/00 73/23.41 |
| 8,663,581 B2* | 3/2014 | Fu ....................... | G01N 1/2202 422/50 |
| 2004/0056016 A1* | 3/2004 | Tian .................... | F27B 17/0025 219/408 |
| 2005/0037513 A1 | 2/2005 | Ivancic et al. | |
| 2006/0099718 A1 | 5/2006 | Tipler et al. | |
| 2007/0275478 A1* | 11/2007 | Taranenko ............. | G01N 1/40 436/175 |
| 2010/0186481 A1* | 7/2010 | Schmidt ............... | G01N 30/12 73/23.42 |
| 2011/0126609 A1* | 6/2011 | Kawarai ............... | G01N 30/14 73/23.35 |

FOREIGN PATENT DOCUMENTS

| | | |
|---|---|---|
| EP | 2 028 485 A1 | 2/2009 |
| WO | 2007/044473 A2 | 4/2007 |

OTHER PUBLICATIONS

International Search Report dated Jun. 5, 2013 in PCT/EP2013/056798 filed Mar. 28, 2013.
Preliminary Search Report dated Jan. 25, 2013 in French Patent Application No. FR 1252850 filed Mar. 29, 2012.
Mingxiao Li, et al., "Preconcentration and Analysis of Trace Volatile Carbonyl Compounds" Analytical Chemistry, vol. 84, No. 3, XP055028949, Feb. 7, 2012, pp. 1288-1293.
Bassam Alfeeli, et al., "MEMS-based multi-inlet/outlet preconcentrator coated by inkjet printing of polymer adsorbents" Sensors and Actuators B, vol. 133, No. 1, XP022824172, Jul. 28, 2008, pp. 24-32.
U.S. Appl. No. 14/438,711, filed Apr. 27, 2015, Ricoul.
U.S. Appl. No. 14/389,051, filed Sep. 29, 2014, Ricoul.
Preliminary Search Report dated Jan. 30, 2013 in French Patent Application No. 1252850 (with English translation of categories of cited documents).
E.H.M. Camara, et al., "Micro gas preconcentrator in porous silicon filled with a carbon absorbent" Sensors and Actuators B: Chemical, vol. 148, 2010, pp. 610-619.
Bassam Alfeeli, et al., "Evaluation of Tenax TA thin films as adsorbent material for micro preconcentration applications" Microchemical Journal, vol. 95, 2010, pp. 259-267.
A. Fonverne, et al., "In situ synthesized carbon nanotubes as a new nanostructured stationary phase for microfabricated liquid chromatographic column" Sensors and Actuators B, vol. 129, 2008, pp. 510-517.
Heather L. Lord, et al., "Fundamentals and applications of needle trap devices: A critical review" Analytica Chimica Acta, vol. 677, 2010, pp. 3-18.

\* cited by examiner

DEVICE AND METHOD FOR EXTRACTING COMPOUNDS CONTAINED IN A LIQUID SAMPLE WITH A VIEW TO ANALYSING THEM

TECHNICAL FIELD AND PRIOR ART

This invention relates to a device and a method of extracting analytes contained in a liquid for their analysis, particularly for their analysis by gas phase chromatography. This invention also relates to a system for analysing analytes contained in a liquid using such an extraction device.

"Analytes" refer to volatile organic compounds present in a liquid matrix.

When analysing analytes contained in a liquid using a gas phase chromatography column, analytes are extracted and concentrated before the analysis is made.

There are several techniques for extracting and concentrating analytes contained in a liquid:

One of these techniques makes use of fibres (Solid Phase MicroExtraction—SPME) or bars (Stir Bar Solid Extraction—SBSE) or Needle Trap Devices (NTD). Fibre is a consumable comprising an adsorbing phase that captures a chemical species when it is dipped in the analysed solution. The fibre is dried and is placed at the inlet to a chromatography column injector. The adsorbed chemical species is then desorbed and transferred in the chromatography column. These different steps are carried out by automatons. Nevertheless, the first step is to draw off samples in flasks.

This type of automaton is usually large and expensive.

In the case of portable chromatography devices, extraction on fibres is made manually and the fibre is introduced into the column manually.

Furthermore, the collection area is relatively small. This technique is then not as sensitive.

Another technique uses the "Purge and Trap" method in which automatons bubble gas inside sampling flasks, such that analytes in the solution are captured by the gas bubble. Bubbles are entrained in a cold trap, in which molecules trapped in the bubbles condense. Then, the cold trap is heated to desorb the analytes by thermodesorption, and the analytes are transferred to a chromatography column. This technique has the disadvantages that a surface has to be cooled and this surface with the trapped molecules has to be displaced manually to connect it to the inlet to the column.

There is a technique for the extraction of analytes contained in a gas that makes use of a silicon micro preconcentrator in which a gas is circulated containing the analytes for example air to quantify pollutants, and the analytes are adsorbed on the silicon. The preconcentrator outlet is directly connected to the detection device. The analytes are then transferred after desorption to the detection device by a carrier gas flow. This technique is described for example in document written by Camara, E. H. M., et al., *Micro gas preconcentrator in porous silicon filled with a carbon absorbent. Sensors and Actuators, B: Chemical,* 2010. 148(2): p. 610-619.

This technique cannot be used for the extraction and concentration of analytes contained in a liquid matrix. If the detection device is a gas phase chromatography column, the liquid matrix circulating through the preconcentrator to adsorp analytes would also circulate in the column. However, circulation of liquid in the column would degrade the stationary phase of the column and the separation quality would be lower.

PRESENTATION OF THE INVENTION

Consequently, one purpose of this invention is to provide a device and a method for extraction of analytes contained in a liquid matrix allowing automatic analysis and enabling a gas phase chromatography analysis without degradation of the column.

The purpose mentioned above is achieved by an extraction device comprising a zone provided with an adsorption surface, supply to said zone being either a liquid containing the analytes or a drying gas or a carrier gas, an evacuation outlet from said zone, said outlet possibly being connected to either an analysis device or to a collection zone.

The device operates in three steps: the supply inlet is configured so that liquid circulates in the extraction zone and the evacuation outlet is configured to direct liquid to the collection zone, and the analytes are then adsorbed on the surface. The supply inlet is then configured so that drying gas circulates in the extraction zone and the evacuation outlet is configured to that the drying gas is sent to the collection zone. Finally, the supply inlet is configured to make the carrier gas circulate in the extraction zone and the evacuation outlet is configured to direct the carrier gas to the analysis device, the carrier gas transporting the desorbed analytes. Thus, in the case of a gas phase chromatography column analysis, no liquid circulates in the column.

The extraction zone comprises microstructures on which the analytes are adsorbed. The microstructures are spaced from each other by a distance advantageously between 10 µm and 50 µm, and the total volume of the extraction zone is advantageously less than 20 µl.

The choice of the microstructure spacing can give a sufficiently large capture area formed by the surface of microstructures while limiting pressure losses in the liquid circulating in the extraction zone. Thus, a liquid flow equal to at least 100 µl/min can be obtained while applying a pressure of the order of about ten bars and not more than a few tens of bars. Furthermore, with a volume of the extraction zone smaller than 20 µl, the analytic device, for example a micro-chromatography column, is not saturated in volume.

Thus with the invention, analytes contained in a liquid sample can be analysed, for example an analytic device of a gas flow with a sufficiently fast analysis rate, a large capture area that improves the sensitivity of the analysis without any risk of saturating the analytic device in volume.

Preferably, automatic switching of supplies and evacuations can be provided.

Advantageously, the extraction-desorption zone comprises thermodesorption means, preferably heating means.

The carrier gas is preferably also the drying gas.

Furthermore according to the invention, the concentration of an analyte of interest in a liquid solution can be determined without requiring any manual operation, making use of a compact and portable automatic online device.

Appropriate programming can be used to perform successive analyses: the concentration of the analyte of interest in the liquid sample can then be monitored automatically.

If a portable module is available, then several modules can be placed in the environment.

Finally, the device may advantageously be made of silicon using microelectronic techniques, which can reduce the cost.

The subject-matter of this invention is then a device for extraction of at least one analyte contained in a liquid sample comprising:
- an extraction and desorption zone of said analyte with a stationary phase called the extraction zone,
- at least one supply inlet to the extraction zone,
- at least one extraction outlet from the desorption zone
- first connection switching means connected to the supply inlet and that will be connected to a tank containing said liquid sample and to at least one gas source to connect the supply inlet with either the tank of said liquid sample or the gas source, second connection switching means connected to the evacuation outlet and that will be connected to a collection tank and to a device for analysis of said analyte, to connect the evacuation outlet with either the collection tank or the analysis device, desorption assistance means, a control unit for said first and second connection switching means such that when the first connection switching means allow supply of the liquid sample to the extraction zone through the supply inlet, the second connection switching means allow evacuation to the collection tank through the evacuation outlet.

The extraction zone comprises microstructures extending from a bottom end to a top end, and a stationary phase supported by said microstructures, said microstructures being spaced from each other at a distance equal to between 10 μm and 50 μm, and said extraction zone having a total volume of less than 20 μl.

The desorption assistance means may for example be means of heating the extraction zone so as to provoke thermodesorption of the analytes. The heating means advantageously increase the temperature in the extraction zone by at least 10° C./s.

The microstructures can be micropillars.

For example, the extraction device comprises a box with a bottom and a lid, the absorption zone being made in said bottom and closed by the lid. The bottom is preferably made from a material with good thermal conduction.

The control unit may also control desorption assistance means.

For example, the device is made using a microelectronic method.

Advantageously, the control unit is such that:
during a first operating step, it controls the first and second connection switching means such that the extraction zone is supplied with liquid sample and said liquid sample is evacuated to the collection tank,
during a second operating step, it controls the first and second connection switching means such that the extraction zone is supplied with gas through the second supply inlet and said gas is evacuated to the storage tank,
during a third operating step, it controls the desorption assistance means and the first and second connection switching means such that the extraction zone is supplied with gas through the third supply inlet and said gas is evacuated to the analysis device.

Another subject-matter of this invention is an analysis system comprising an extraction device according to the invention, at least one gas source, a tank that will contain the liquid sample to be analysed, an analysis device and a collection tank.

For example, the analysis device is a gas phase chromatography system.

The analysis system may comprise a direct connection between the gas source and the chromatography column and third connection switching means such that when the first switching means allow supply of the extraction zone by the gas source, said third connection switching means interrupt the direct supply of the gas source to the gas phase chromatography column.

Another subject-matter of this invention is a method of extracting at least one analyte contained in a liquid sample comprising the following steps:

a) start circulation of said liquid sample through the extraction zone with a stationary phase, said analyte being adsorbed in the extraction zone, said liquid sample being evacuated to a collection tank, b) interruption of said circulation of the liquid sample, c) start circulation of a gas through the extraction zone to dry said extraction zone, said gas being evacuated to said collection zone d) interruption of said gas circulation, e) start circulation of a gas through the extraction zone of said analyte and desorption of said analyte, In step e), the extraction zone may be heated to provoke desorption.

The gas circulating in step c) and the gas circulating in step e) are advantageously the same gas and form a carrier gas.

For example, step c) lasts between 1 s and a few minutes, preferably between 1 s and 60 s, and desorption of step e) lasts between 1 s and 10 s.

Another subject-matter of this invention is a method of analysing at least one analyte contained in a liquid comprising steps a) to e) of the extraction method according to the invention, and a step f) after step e) in which said analyte is analysed.

Step f) may be gas phase chromatography.

Advantageously, the liquid sample is an aqueous solution and the analytes are volatile organic compounds.

BRIEF DESCRIPTION OF THE DRAWINGS

This invention will be better understood after reading the following description and the appended drawings in which.

DETAILED PRESENTATION OF PARTICULAR EMBODIMENTS

Figure 1:
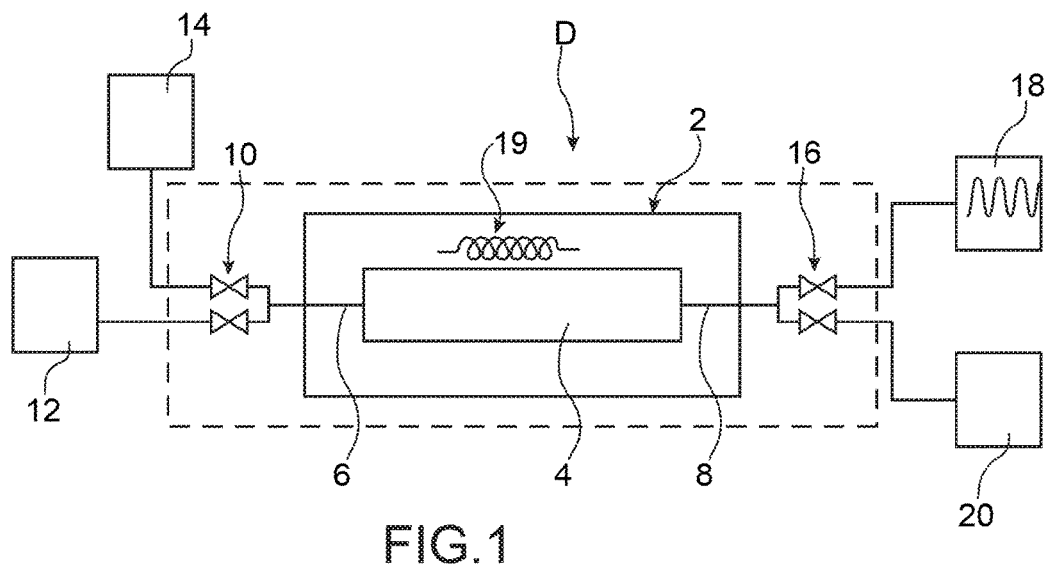
FIG. 1 is a diagrammatic view of an example of an extraction and concentration device.

FIG. 1 shows a diagrammatic view of an example of an extraction and concentration device according to this invention.

Device D comprises a module 2 containing an absorption and desorption zone 4. The module comprises a supply orifice 6 and an evacuation orifice 8 for supplying the extraction zone 4 with fluid and evacuation from the extraction zone 4.

For simplification reasons, the extraction, adsorption and desorption zone 4 will be referred to as the "extraction zone 4" in the remainder of this description.

For example, the module 2 is formed from a box with a bottom and a lid, the extraction zone 4 being made in the bottom of the box, and the module is closed and sealed by the lid.

The extraction zone 4 is formed by one or several channels on the surface of which analytes will be adsorbed and desorbed. The extraction zone 4 preferably has a large surface to volume ratio, so that analytes can be adsorbed efficiently.

The extraction zone comprises microstructures. These microstructures preferably extend from a bottom end to a top end of the device. These microstructures are for example micropillars or microcolumns with a constant cross-section between the bottom end and the top end. This shape has the advantage that it limits disturbances in the flow and is compatible with microfabrication methods.

The stationary phase is supported by the microstructures. These microstructures increase the surface area on which analytes will be adsorbed, which increases the sensitivity of the analysis.

The spacing between microstructures is advantageously between 10 µm and 50 µm, and preferably between 10 µm and 30 µm.

The extraction zone then has a sufficiently large capture area while limiting pressure losses in the liquid flow. Thus, a flow of at least 100 µl/minute can be obtained by applying a pressure of about ten bars to the liquid, and not more than a few tens of bars and less than 100 bars. The means of applying pressure to the liquid can then be compact.

Furthermore, the total volume of said extraction zone is advantageously less than 20 µl, and preferably less than 10 µl. This avoids volume saturation of the analytic device, for example the chromatography column.

A large volume of a liquid sample can be processed in a short time with the extraction device, because of the flow that can be obtained due to the structure of the extraction zone, and precise analyses can be made because volume saturation of the analytic device is avoided.

For example, the height of the microstructures is advantageously between 50 µm and 400 µm, and preferably between 100 µm and 300 µm.

If the height of the microstructures were too small, the length or width of the extraction zone would have to be increased relative to its height for the same total volume, which would increase pressure losses. And if the microstructures were too high, the shape of the microstructures could no longer be sufficiently well controlled with the microfabrication methods used.

The surface of the extraction zone 4 is covered with an adsorbent or stationary phase adapted to the analytes to be analysed. For example, it could consist of liquid or porous polymers such as PDMS (polydimethylsiloxane), Tenax, DVB, Carboxen . . . , carbon nanotubes, active carbon or porous silicon. For a PDMS deposit, its thickness would be of the order of a few hundred nm. This phase is deposited by known methods for making gas phase chromatography column. The stationary phase is then in the form of a film with a thickness of between 50 nm and a few µm, for example 2 µm or 3 µm.

The Surface area to Volume ratio in the extraction zone 4 may be as high as $0.6 \, \mu m^{-1}$ and $0.8 \, \mu m^{-1}$, but it may be even higher in the case of a nanostructured extraction zone.

For example, the micropillars have a square cross-section with a side of 10 µm and a height of 100 µm, and the spacing between them is equal to 10 µm.

The device also comprises upstream switching means 10 to connect the supply orifice 6 either to a tank 12 containing the liquid to the analysed, or to a gas source 14 on the upstream side of the extraction zone 4. The upstream switching means 10 may for example a pair of valves. These valves are so-called stop valves because they change from an open position to a closed position.

As we will see in the following, the gas is a carrier gas, for example helium, air, nitrogen or hydrogen.

Furthermore as we will see in the description of operation of the device, the device may be connected to two different gas sources.

The device also comprises downstream switching means 16 to connect the evacuation orifice 8 to either an analysis device 18, or a collection tank 20 on the downstream side of the extraction zone 4. The downstream connection means 16 may for example be formed by a pair of stop valves as described above.

This example embodiment uses two pairs of valves, a supply orifice and an evacuation orifice, which simplifies the device.

Such pairs of stop valves are controlled such that the two valves are not opened simultaneously.

Advantageously, these stop valves may be in the form of MEMS type devices, which results in better integration when the device is made in an Si type substrate.

According to one variant, each pair of stop valves located upstream or downstream from the extraction zone 4 may be replaced by valves called 4-way valves, well known in the field of chromatography. When a 4-way valve is used upstream from the extraction zone 4, then forming the upstream switching means 10, the fourth orifice is connected to an evacuation. When a 4-way valve is used downstream from the extraction zone 4, then forming the downstream switching means 16, the fourth orifice is connected to the carrier gas of the analysis system.

Preferably, the device comprises a control unit controlling the switching means 10, 16 so as to obtain automated operation of the device. Nevertheless it would also be possible to control the switching means 10, 16 manually.

Injection means 22 between the liquid tank 12 and the extraction zone 4 are provided, for example a pump or a syringe pusher. Advantageously, a micro-pump is used that can be integrated into the device when the device is made in an Si type substrate.

For example, the connection tubes may be formed by capillaries for which the typical diameter is a few 100 µm, typically 50 µm to 500 µm. As a variant, it would be possible to envisage making a system integrated on a silicon substrate, circulation between the tanks and the extraction zone 4 then passing through micro-channels etched in the silicon.

Advantageously, the device D comprises means 19 for assisting desorption. For example, it might consist of means of heating the extraction zone 4 so as to provoke a temperature increase of the surface and to provoke thermodesorption of the analytes. Preferably, these heating means provoke a fast increase in the surface temperature, for example of the order of 10° C./s in order to obtain fast desorption of analytes and fast transfer to the analysis device. For example, these heating means make use of the external Peltier effect or an electrical resistance integrated into the box or in contact with it. For example, the electrical resistance may be formed by a metal track, for example a Platinum track made in the surface of the zone. Advantageously, the heating means are also controlled by the control unit. Thus, after having switched the supply orifice to the carrier gas supply and the evacuation orifice to the analysis device, the control unit automatically provokes desorption of the analytes.

Advantageously, the microstructures are made in a single piece with the bottom of the box, for example by etching. The material used for the bottom of the box and the microstructures is advantageously a good thermal conductor to facilitate a fast temperature rise during the thermodesorption phase.

For example, the bottom of the box is made of silicon. It can also be etched with a very wide variety of patterns and it can be used to make large scale objects which makes it easy to manufacture microstructures in the extraction zone 4.

The device and more particularly the extraction zone 4 may be made using microelectronic methods that currently use silicon The lid may be transparent, for example made of glass, which enables a display of the extraction zone 4. For example, the lid is fixed on the bottom by molecular bonding or anodic bonding.

Figure 2:
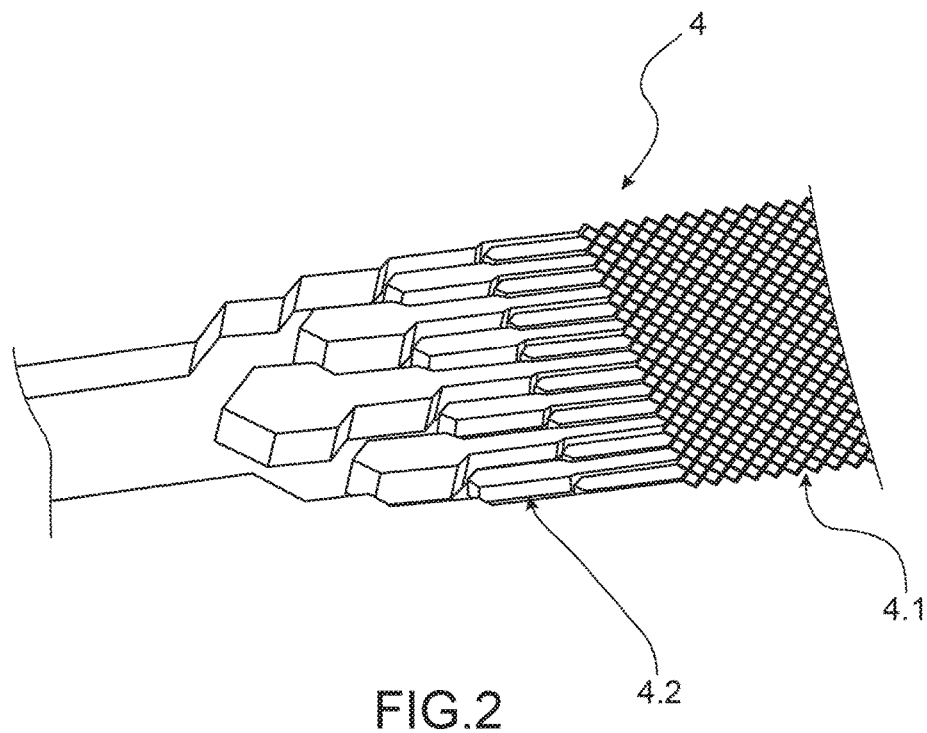
FIG. 2 is a partial top view of an example structure of the extraction zone.

FIG. 2 shows an example of a structure of an extraction zone 4 comprising a microstructured portion 4.1 in which adsorption and desorption take place, and an upstream supply zone 4.2 formed by a tree structure of channels starting from the supply orifice 6 to the microstructured portion 4.1 that gives a uniform distribution of liquid or gas in the microstructured portion 4.1. The extraction zone 4 also comprises a downstream evacuation zone (not shown) presenting a tree structure to collect the fluid to the evacuation orifice.

Figure 3A:
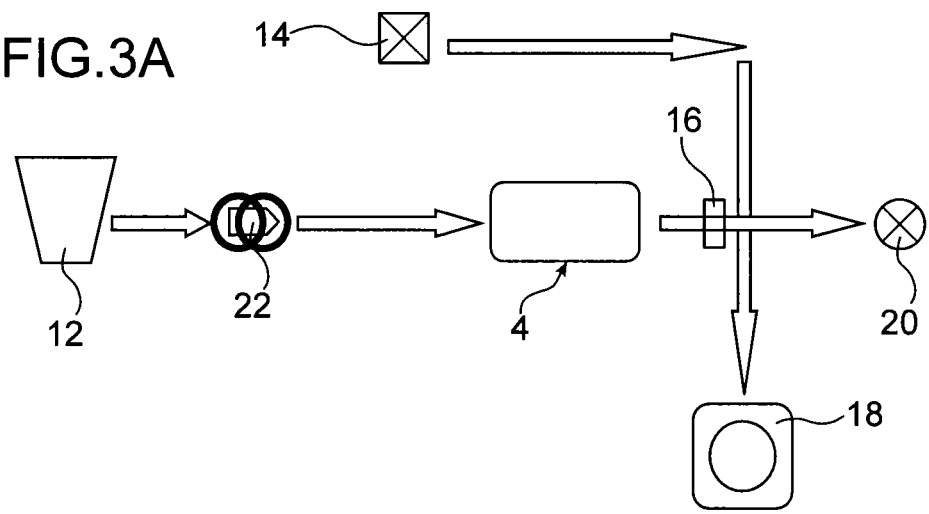
FIGS. 3A to 3C are diagrammatic views of the different operating steps of an analysis system according to the invention.

FIG. 3A shows an example of an analysis system according to the invention comprising an extraction device as shown in FIG. 1, a liquid sample tank and a carrier gas source, for example helium, both connected to two inlets to the upstream switching means 10. The system also comprises an analysis device, for example a gas phase chromatography system and a collection tank, both connected to two outlets from the downstream switching means 16.

Figure 3B:
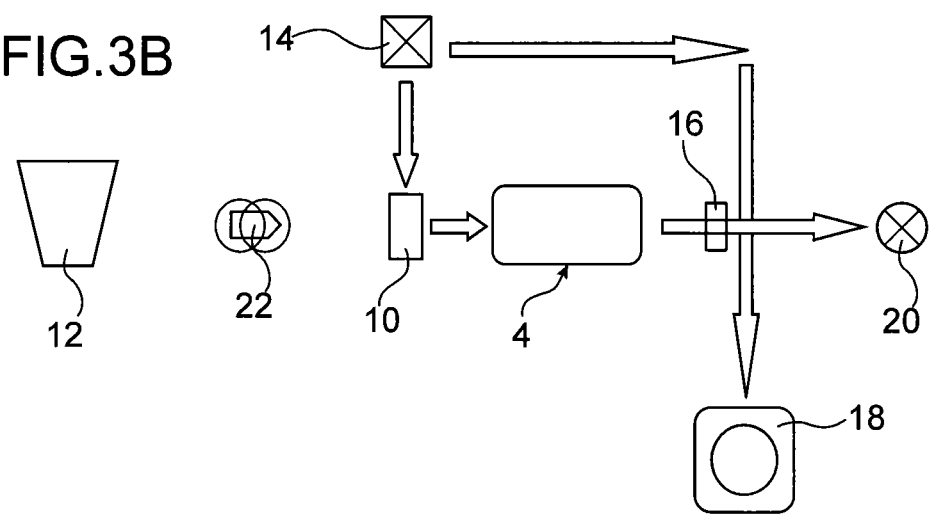
Figure 3C:
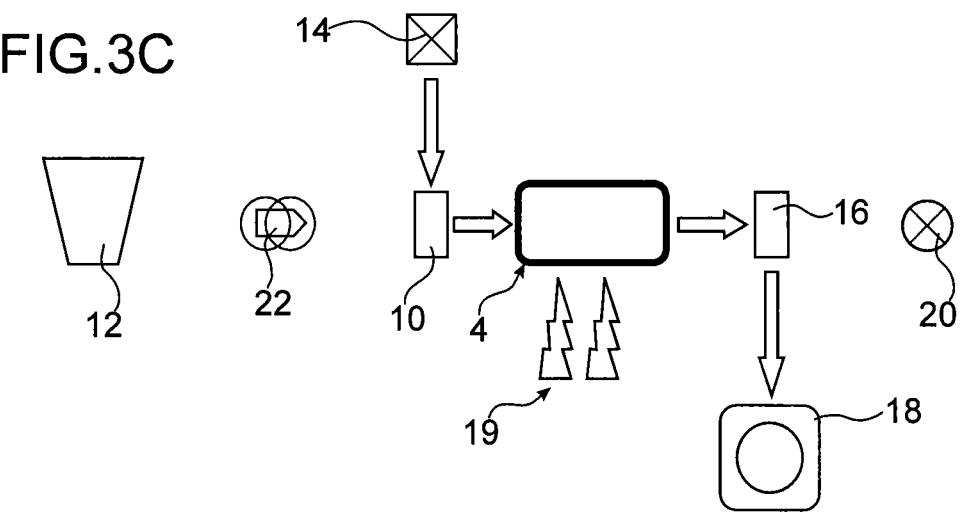

We will now explain operation of the extraction device and the analysis system with reference to FIGS. 3A to 3C.

We will consider the example in which the liquid to be analysed is an aqueous solution.

The fluid circulation is symbolised by arrows.

For example, the extraction zone 4 comprises micropillars with a square section with a side dimension equal to 10 μm, 100 μm high, at a spacing from each other of 10 μm and extending over a length of 4 cm and a width of 180 μm. The equivalent cross section is 180 μm×100 μm.

During a first operating phase diagrammatically shown in FIG. 3A, the supply orifice 6 is connected to the liquid tank and the evacuation orifice is connected to the collection tank.

Preferably, the column is scavenged by the carrier gas, which avoids disturbance of the equilibrium when the analytes are injected into the column. The carrier gas flow in the column may for example be of the order of 1 ml/min.

The liquid is injected into the extraction zone 4 by means of the pump, for example at a flow of 10 μl/min to 500 μl/min. The analytes are adsorbed on the surface of the extraction zone 4.

After passing through the zone, the liquid is evacuated into the storage tank. During the first phase, the analytes are extracted from the liquid by adsorption and are concentrated in the extraction zone 4.

For example, the duration of this first phase is between 10 minutes and 200 minutes, and with the invention a few tens of ml can be processed at the rates mentioned above while maintaining a reasonable analysis time.

The second phase begins when a sufficient quantity of liquid has been processed, for example between 5 ml and 100 ml, the upstream connection means 10 are then switched to connect the inlet orifice to the carrier gas source. The state of the evacuation connection means 16 is not changed.

The effect of circulating the carrier gas through the zone is to dry the surface of the extraction zone 4 so as to eliminate water and mineral contaminants so that they are not sent into the column. After passing through the column, the gas contains water and/or mineral contaminants and is evacuated to the collection tank.

Thus, no liquid phase enters into the column. The temperature during this drying phase is such that desorption of the analytes is negligible. The drying temperature is typically the ambient temperature, in other words less than 40° C. At a higher temperature, there is a risk of a significant quantity of molecules being desorbed. Therefore it is preferable to remain below the boiling point of the analytes to assure that they do not diffuse in the drying gas.

For example, the carrier gas flow is between 1 ml/min and 10 ml/min.

Circulation of carrier gas through the column is maintained during this phase.

This second phase can last between a few seconds and a few minutes, preferably between 30 s and 300 s.

As a variant, it would be possible for the gas circulating in the extraction zone 4 for drying to be different from the carrier gas used to transport analytes in the column.

During a third phase, the evacuation connection means 16 are switched to connect the outlet orifice from the extraction zone 4 to the column inlet. Furthermore, the carrier gas from the column now circulates through the extraction and concentration device rather than directly as in the first and second phases.

The heating means are activated causing thermodesorption of the analytes that are then transferred by the carrier gas as far as the column. The duration of the heating phase is between 1 s and 10 s. In general, the temperature to be reached during thermodesorption will then be between 100° C. and 300° C., the preferred range being between 200° C. and 300° C.

With the invention, the extraction may be done continuously, automatically and without manual sampling.

Furthermore, the sample preparation step may be integrated onto a small device so that a complete portable analysis device can be made.

Furthermore, by using a microstructured extraction and desorption zone the extraction time is reduced and the extraction efficiency is improved.

The invention is applicable to all liquids and more particularly aqueous solutions comprising organic compounds and thermodesorption is particularly efficient for this type of compound.

This device can be used to extract VOCs (volatile organic compounds) such as alcohols, BTEX (benzene, toluene, ethylbenzene, xylene) that are atmospheric pollutants, pesticides, etc.

For example, the device according to the invention associated with a gas phase chromatography system can be used for analysis of VOCs in drinking water distribution networks, and for control of industrial processes (for example in the pharmaceutical field, microelectronics, etc.), process control in water retreatment.

The invention claimed is:

1. An extraction device for extraction of at least one analyte contained in a liquid sample, comprising:
    an extraction and desorption zone of the at least one analyte with a stationary phase as the extraction zone;
    at least one supply inlet to the extraction zone;
    at least one extraction outlet from the extraction zone;
    a first connection switch connected to the at least one supply inlet, and configured to connect to a tank containing the liquid sample and to at least one gas source, and to connect the at least one supply inlet with either the tank containing the liquid sample or with the at least one gas source;
    a second connection switch connected to an evacuation outlet, and configured to connect to a collection tank and to a device configured to analyze the at least one analyte, and to connect the evacuation outlet with either the collection tank or with the analysis device;
    a desorption assistance means; and a controller for the first and second connection switches, configured such that when the first connection switch allows a supply of the liquid sample to the extraction zone through the at least one supply inlet, the second connection switch allows evacuation to the collection tank through the evacuation outlet, wherein the extraction zone comprises microstructures extending from a bottom end to a top end, and the stationary phase is supported by the microstructures, the microstructures being spaced from each other at a distance equal to between 10 µm and 50 µm, and wherein the extraction zone has a total volume of less than 20 µl.

2. The device according to claim 1, wherein the spacing between the microstructures is between 10 µm and 30 µm.

3. The device according to claim 1, wherein the extraction zone has a total volume of less than 10 µl.

4. The device according to claim 1, wherein the desorption assistance means comprises a heater of the extraction zone configured to provoke thermodesorption of the at least one analyte.

5. The device according to claim 4, wherein the heater is configured to increase a temperature in the extraction zone at a rate of at least 10° C./s.

6. The device according to claim 1, wherein the microstructures are micropillars.

7. The device according to claim 1, wherein the bottom end and the microstructures are made of a single piece and are made from a thermally conductive material.

8. The device according to claim 1, further comprising a box with a bottom forming the bottom end and a lid forming the top end, the extraction zone being made in the bottom and closed by the lid.

9. The device according to claim 1, wherein the controller is also configured to control the desorption assistance means.

10. The device according to claim 1, wherein the device is at least partially a microelectromechanical device.

11. The device according to claim 1, wherein the controller is further configured to:
during a first operation step, control the first and second connection switches such that the extraction zone is supplied with the liquid sample and the liquid sample is evacuated to the collection tank,
during a second operation step, control the first and second connection switches such that the extraction zone is supplied with gas through a second supply inlet and the gas is evacuated to the collection tank, and
during a third operation step, control the desorption assistance means and the first and second connection switches such that the extraction zone is supplied with the gas through the second supply inlet and the gas is evacuated to the analysis device.

12. An analysis system, comprising:
an extraction device according to claim 1;
at least one gas source;
a tank that will contain the liquid sample to be analysed;
the analysis device; and
a collection tank.

13. The analysis system according to claim 12, wherein the analysis device is a gas phase chromatography system.

14. The analysis system according to claim 12, further comprising a direct connection between the at least one gas source and a chromatography column and a third connection switch such that when the first connection switch allows supply of the extraction zone by the at least one gas source, the third connection switch interrupts direct supply of the at least one gas source to the gas phase chromatography column.

15. A method of extracting at least one analyte contained in a liquid sample using an extraction system including at least one gas source, a tank that will configured to contain the liquid sample to be analysed, an analysis device, a collection tank, and an extraction device configured to extract the at least one analyte contained in the liquid sample, the extraction device including:
an extraction and desorption zone of the at least one analyte with a stationary phase as the extraction zone,
at least one supply inlet to the extraction zone,
at least one extraction outlet from the extraction zone,
a first connection switch connected to the at least one supply inlet, and that will be connected to a tank containing the liquid sample and to at least one gas source, to connect the at least one supply inlet with either the tank of the liquid sample or the at least one gas source,
a second connection switch connected to the evacuation outlet, and configured to connect to a collection tank and to the analysis device configured to analyze the at least one analyte and to connect the evacuation outlet with either the collection tank or with the analysis device,
a desorption assistance means, and
a controller for the first and second connection switches, configured such that when the first connection switch allows a supply of the liquid sample to the extraction zone through the at least one supply inlet, the second connection switch allows evacuation to the collection tank through the evacuation outlet,
wherein the extraction zone comprises microstructures extending from a bottom end to a top end, and the stationary phase is supported by the microstructures, the microstructures being spaced from each other at a distance equal to between 10 µm and 50 µm, and
wherein the extraction zone has a total volume of less than 20 µl; and
the method comprising:
a) starting circulation of the liquid sample through the extraction zone with the stationary phase, the at least one analyte being adsorbed in the extraction zone, the liquid sample being evacuated to a collection tank;
b) interrupting the circulation of the liquid sample;
c) starting circulation of a gas through the extraction zone to dry the extraction zone, the gas being evacuated to the collection tank;
d) interrupting the gas circulation; and
e) starting circulation of the gas through the extraction zone to provoke desorption of the at least one analyte.

16. The method according to claim 15, wherein in step e), the extraction zone is heated to provoke the desorption.

17. The method according to claim 15, wherein the gas circulating in step c) and the gas circulating in step e) are a same gas and form a carrier gas.

18. The method according to claim 15,
wherein step c) lasts between 1 s and a few minutes, or between 1 s and 60 s, and
wherein desorption of step e) lasts between 1 s and 10 s.

19. The method according to claim 15, further comprising, after step e), a step f) of analyzing the at least one analyte.

20. The method according to claim 19, wherein the analyzing of step f) is a gas phase chromatography.

21. The method according to claim 15, wherein the liquid sample is an aqueous solution and the at least one analyte is a volatile organic compound.

* * * * *